United States Patent [19]

Findlay et al.

[11] Patent Number: 5,196,305
[45] Date of Patent: Mar. 23, 1993

[54] DIAGNOSTIC AND AMPLIFICATION METHODS USING PRIMERS HAVING THYMINE AT 3' END TO OVERCOME PRIMER-TARGET MISMATCH AT THE 3' END

[75] Inventors: John B. Findlay; Lynn Bergmeyer, both of Rochester, N.Y.

[73] Assignee: Eastman Kodak Company, Rochester, N.Y.

[21] Appl. No.: 406,221

[22] Filed: Sep. 12, 1989

[51] Int. Cl.[5] .............................................. C12Q 1/68
[52] U.S. Cl. ................................... 435/6; 435/91;
435/805; 435/948; 436/501; 436/811; 536/27;
935/6; 935/17; 935/19; 935/78; 935/88
[58] Field of Search ................ 435/6, 91, 805, 948;
436/501, 811; 536/27; 935/6, 17, 19, 78, 88

[56] References Cited

U.S. PATENT DOCUMENTS

| | | | |
|---|---|---|---|
| 4,656,127 | 4/1987 | Mundy | 435/6 |
| 4,683,195 | 7/1987 | Mullis et al. | 435/6 |
| 4,683,202 | 7/1987 | Mullis | 435/91 |
| 4,794,075 | 12/1988 | Ford et al. | 435/6 |
| 4,800,159 | 1/1989 | Mullis et al. | 435/172.3 |
| 4,851,331 | 7/1989 | Vary et al. | 435/6 |
| 4,889,818 | 12/1989 | Gelfand et al. | 435/194 |

FOREIGN PATENT DOCUMENTS 0229701  7/1987  European Pat. Off. .

OTHER PUBLICATIONS

Kwok et al., (1990) Nucleic Acids Res., vol. 18, No. 4, pp. 999–1005.
Wu et al., Proc. Natl. Acad. Sci. USA, 86, pp. 2757–2760, Apr., 1989.
Newton et al., Nucl. acids res., 17(7), pp. 2503–2516, Apr., 1989.
Ehlen et al., Biochem. Biophys. Res. Comm., 160(2), pp. 441–447, Apr. 1989.
Cotton et al., Proc. Natl. Acad. Sci. USA, 85(12), pp. 4397–4401, 1988.
Petruska et al., Proc. Nat'l. Acad. Sci.: USA, 85, pp. 6252–6256, 1988.
Patel et al., Fed. Proc. Fed. Am. Soc. Exp. Biol., 43 (11), pp. 2663–2670, (1984), Abstract Only CA 102:2120n, 1985.
Okayama et al., J. Lab. Clin. Med., 114(2), pp. 105–113 (Aug., 1989).

Primary Examiner—Margaret Moskowitz
Assistant Examiner—Ardin H. Marschel
Attorney, Agent, or Firm—J. Lanny Tucker

[57] ABSTRACT

Methods for amplifying and detecting a predetermined target nucleic acid in a biological specimen are accomplished even where there is a mismatch in a single position between a primer and the target nucleic acid. The mismatch is located at or near the 3' end of the primer. Such a mismatch is overcome using a primer having a nucleotide with a thymine base at the position of the mismatch. The use of such primers is most likely to prime the target and form primer extension products. This method is particularly useful for detection of a nucleic acid sequence which is not fully known, or where there is considerable heterogeneity in DNA target from patient samples.

16 Claims, 3 Drawing Sheets

CORRESPONDING TEMPLATE BASE

| | A | C | G | T |
|---|---|---|---|---|
| A | − 1.5 | + 3.0 | − 0.3 | + 3.0 |
| C | + 1.8 | − 1.5 | + 3.5 | + 1.5 |
| G | − 0.3 | + 3.8 | − 1.0 | + 3.0 |
| T | + 2.3 | + 3.0 | + 2.3 | + 3.5 |

PRIMER 3' END NUCLEOTIDE

CORRESPONDING TEMPLATE BASE

| | A | C | G | T |
|---|---|---|---|---|
| A | − 1.5 | + 3.0 | − 0.3 | + 3.0 |
| C | + 1.8 | − 1.5 | + 3.5 | + 1.5 |
| G | − 0.3 | + 3.8 | − 1.0 | + 3.0 |
| T | + 2.3 | + 3.0 | + 2.3 | + 3.5 |

PRIMER 3' END NUCLEOTIDE

FIG. 1

CORRESPONDING TEMPLATE BASE

| | A | C | G | T |
|---|---|---|---|---|
| A | −<br>0.8 | −<br>3.5 | −<br>0.0 | +<br>3.5 |
| C | +<br>3.3 | −<br>0.0 | +<br>3.3 | +<br>3.3 |
| G | −<br>0.0 | +<br>3.5 | −<br>0.5 | −<br>2.8 |
| T | +<br>2.8 | +<br>3.3 | +<br>3.8 | +<br>2.3 |

PRIMER 3' END NUCLEOTIDE

FIG. 2

CORRESPONDING TEMPLATE BASE

| PRIMER 3' END NUCLEOTIDE | | A | C | G | T |
|---|---|---|---|---|---|
| | A | −<br>1.5 | +<br>3.5 | −<br>0.0 | +<br>4.5 |
| | C | +<br>3.8 | −<br>0.0 | +<br>2.5 | +<br>4.0 |
| | G | −<br>0.0 | +<br>3.5 | −<br>1.5 | +<br>3.5 |
| | T | +<br>3.8 | +<br>3.5 | +<br>3.0 | +<br>3.3 |

FIG. 3

DIAGNOSTIC AND AMPLIFICATION METHODS USING PRIMERS HAVING THYMINE AT 3' END TO OVERCOME PRIMER-TARGET MISMATCH AT THE 3' END

FIELD OF THE INVENTION

The present invention relates to a method for amplification of a predetermined nucleic acid. It is particularly directed to a method for amplification and detection of that nucleic acid using a certain primer and the polymerase chain reaction. The invention can be used to detect nucleic acids associated with genomic, bacterial or viral DNA or RNA.

BACKGROUND OF THE INVENTION

Nucleic acid probe technology has developed rapidly in recent years as researchers have discovered its value for detection of various diseases, organisms or genetic features which are present in very small quantities in a test sample. The use of probes is based upon the concept of complementarity. In DNA the two strands are bound to each other by hydrogen bonds between complementary nucleotides (also known as nucleotide pairs).

The DNA complex is normally stable, but the strands can be separated (or denatured) by conditions which disrupt the hydrogen bonding. The released single strands will reassociate only with another strand having a complementary sequence of nucleotides. This hybridization process can occur in solution or on a solid substrate. RNA is usually single-stranded. It can also hybridize with another strand or portion thereof which has a complementary sequence of nucleotides.

A target nucleic acid sequence of DNA or RNA of a target organism or cell may be only a small portion of the total strand, so that it is very difficult to detect its presence using most known labeled DNA probes. Much research has been carried out to overcome this problem including improvements in probe sensitivity and synthesis of nucleic acids.

A significant advance in the art is described in U.S. Pat. Nos. 4,683,195 (issued Jul. 28, 1987 to Mullis et al) and 4,683,202 (issued Jul. 28, 1987 to Mullis). Without going into extensive detail, these patents describe an amplification method wherein primers are hybridized to nucleic acid templates in the presence of a polymerization agent (such as a polymerase) and four nucleotide triphosphates, and extension products are formed from the primers. These products are denatured and used as templates in a cycling reaction which amplifies the number and amount of existing nucleic acids to facilitate their subsequent detection. The amplification method can be carried out cyclically as many times as desired to produce a larger quantity of detectable material from a small amount of target nucleic acid sequence.

In the amplification method described above, two primers are used for the target nucleic acid to be amplified. Design of an efficient diagnostic assay based upon the polymerase chain reaction depends greatly on the efficiency with which the primers hybridize with the target nucleic acid. In the best case for amplification, the nucleic acid sequence to be amplified is completely complementary with the primer, at least near the 3' end of the target sequence where extension will occur. Thus, only one primer per strand is needed for effective amplification. It is known from the art that where the target sequence is not entirely known, at least at the 3' end, a collection of primers having all possible codon variations can be used in order to have at least one primer which is completely complementary.

The use of a collection of primers may be used to accomplish the amplification process desired, but it is impractical due to its expense and may be inefficient or ineffective in many instances. The preparation of the collection of random primers is wasteful and leads to the use of competitive non-extending primers. Moreover, the greater the uncertainty of the target nucleotide sequence, the collection of primers needed is greatly enlarged.

Viral genomes, particularly those of RNA viruses and retroviruses, contain multiple base alterations, additions, duplications and deletions. The variability of these viruses has been attributed to the low fidelity and lack of proofreading functions of polymerases responsible for replication (see Steinhauer et al, *Ann. Rev. Microbiol.*, 41, pp. 409–433, 1986). Repeated rounds of infection further increase variability. The effects of such variations in the natural history of infection of a given virus is only beginning to be understood.

Thus, in the detection of heterogeneous DNA from retroviruses, the target nucleic acid is highly variable, and complete identity is not always known. With HIV-I, for example, a variety of sequences in the genome produces a viable virus. Base substitutions are known to occur at random and frequent intervals over the entire genome. Thus, different isolates are likely to have viral DNA which have different nucleic acid sequences which could lead to mismatches with primers thought to be complementary.

Such mismatches will considerably reduce the efficiency of amplification by primers, especially when the mismatch between target and primer occurs at or near the 3' end of the primer. In other words, mismatches lead to a slowing down of the amplification process because the kinetics of priming and primer extension are changed (see for example, Tinoco, Jr., *Proc. Nat. Acad. Sci.(USA)*, 85, 6252, 1988). In the worst case, no amplification will occur as the primer fails to attach to the target, or if it attaches, formation of an extension product is inhibited (that is, the primer "misfires").

It would be desirable to have an efficient means for amplifying and detecting nucleic acids even if there is a mismatch between a targeted sequence of the nucleic acid and a primer at or near the 3' end of the primer.

SUMMARY OF THE INVENTION

The problem noted above with mismatches occurring at the 3' end of the primer is overcome using a method for amplifying a nucleic acid, which method comprises:

A. contacting a specimen comprising a nucleic acid with a primer composition,
   the primer composition consisting essentially of a primer which is complementary to a sequence of the nucleic acid in every position except a single position at or near the 3' end of the primer, resulting in a single mismatch at the single position between the primer and the nucleic acid sequence, the primer having a nucleotide with a thymine base in the position of the mismatch, and B. substantially simultaneously, contacting the specimen with a polymerization agent under conditions such that the nucleic acid is amplified in the resulting mixture.

Moreover, a method for the detection of a nucleic acid comprises:

A. contacting a specimen comprising a nucleic acid with a primer composition, the primer composition consisting essentially of a primer which is complementary to a sequence of the nucleic acid in every position except a single position at or near the 3' end of the primer, resulting in a single mismatch at the single position between the primer and the nucleic acid sequence, the primer having a nucleotide with a thymine base in the position of the mismatch, so as to form hybridized products of the primer and the nucleic acid, B. forming primer extension products in the hybridized products, priming, extending and amplifying the primer extension products, C. separating the resulting primer extension products and contacting them with a detection or capture oligonucleotide probe to form a complementary product, and D. detecting the presence of the complementary product as an indication of the presence of the nucleic acid in the specimen.

The present invention provides methods for rapidly and accurately amplifying or detecting nucleic acids which are present in very small quantities in a test specimen. Moreover, this method can be carried out efficiently where there is a single mismatch in complementarity at or near the 3' end of a primer and a targeted sequence of a predetermined nucleic acid. Overall product yield is not appreciably reduced by such a mismatch when this invention is practiced. Thus, amplification is considerably more efficient in replicating sequences which are variant from isolate to isolate, such as with retroviruses.

These advantages are achieved by using a primer having a nucleotide with a thymine in the position of the mismatch at or near the 3' end. In other words, where a mismatch between target nucleic acid and primer occurs, up to four nucleotides from the 3' end, the primer has a thymine base in that nucleotide position. It has been found that the use of such a primer most readily overcomes such mismatch, and maintains efficient priming and amplification of the target nucleic acid. This invention is particularly useful in the detection of retroviruses, such as HIV-I, where there is extensive heterogeneity within and among infected individuals.

BRIEF DESCRIPTION OF THE DRAWINGS

FIG. 1 is a matrix summary of the amplification results using various 3' end mismatches where a high salt concentration and high hybridization temperature were used in the amplification reaction. It is referred to in Example 1 below.

FIG. 2 is a matrix like FIG. 1 for the results of Example 2 below wherein the amplification reaction was carried out with a low salt concentration.

FIG. 3 is a matrix like FIG. 1 for the results of Example 3 below wherein the amplification reaction was carried out with a high salt concentration and low hybridization temperature.

DETAILED DESCRIPTION OF THE INVENTION

The present invention is directed to the amplification or detection of one or more specific nucleic acid sequences present in one or more predetermined (that is, targeted) nucleic acids in a test specimen. Such samples can include cellular or viral material, hair, body fluids, or other materials containing bacterial, viral or genomic DNA or RNA which can be detected. While the primary purpose of detection would be diagnostic in nature, the invention could also be used to improve the efficiency of cloning DNA or messenger RNA, or for obtaining large amounts of the desired sequence from a mixture of nucleic acids resulting from chemical synthesis.

The invention is especially useful when combined with a chain reaction for producing, in exponential quantities relative to the number of reaction steps involved, at least one predetermined nucleic acid sequence. The product will be a discrete nucleic acid duplex with termini corresponding to the ends of the specific primers employed. Any source of nucleic acid, purified or not, can be utilized as the starting material provided it contains or is suspected of containing the specific nucleic acid targeted for amplification or detection. A mixture of nucleic acids can be employed if desired. The sequence to be duplicated can be a fragment or the entire nucleic acid. Moreover, more than one nucleic acid sequence can be amplified simultaneously by using a set of primers for each sequence to be amplified. The sequences can be in the same or different nucleic acids.

Nucleic acids can be obtained from various sources including plasmids, naturally occurring DNA or RNA from any plant, animal or human source. It may be extracted from various tissues including blood, peripheral blood mononuclear cells, tissues or other sources known in the art. This invention is particularly useful for the amplification and detection of viral DNA, such as from human papilloma viruses, RNA viruses and retroviruses (for example, HIV-I), extracted from fluids and cells infected by the virus where heterogeneity within and among infected individuals is prevalent.

DNA is isolated from the cells in a specimen using any suitable technique, many of which are well known in the art, as long as the technique does not degrade the DNA. For example, it can be extracted from cells using a buffered protease or proteinase K composition at a temperature and pH which reduces the likelihood that the DNA will be degraded, as described, for example by Kan et al, *New Eng. J. Med.*, 297, pp. 1080–1084 (1977) and in *Nature*, 251, pp. pp. 392–393 (1974). Other extraction techniques are described in EP-A-0 145 356 (published Jun. 19, 1985), EP-A-0 240 191 (published Oct. 7, 1987), and EP-A-0 240 191 (published Oct. 7, 1987), and EP-A-0 245 945 (published Nov. 19, 1987), and by Nunberg et al, *Proc. Nat. Acad. Sci. (USA)*, 75(11), pp. 5553–5556, 1978 and Saiki et al, *Bio/Technology*, 3, pp. 1008–1012 (1985).

The extracted DNA can be purified by dialysis, chromatography, affinity capture using complementary nucleic acids or by any other suitable technique readily apparent to one skilled in the art.

Once isolated DNA is obtained, it is subjected to an amplification procedure which produces exponential quantities of the molecule relative to the number of steps involved. It is to be understood that where several DNA molecules are of interest, the amplification process can be used to multiply all of them. The end result is a large number of detectable nucleic acids which can then be subjected to typing procedures for evaluation.

The amplification method generally used is described in considerable detail in U.S. Pat. Nos. 4,683,195 and 4,683,202 (noted above), the disclosures of which are incorporated herein by reference.

As used herein in referring to primers or probes, the term "oligonucleotide" refers to a molecule comprised of two or more deoxyribonucleotides or ribonucleotides, and preferably more than three. The exact size is not critical (except for the probe described below) but depends upon many factors including the ultimate use or function of the oligonucleotide. The oligonucleotide may be derived synthetically or by other methods known in the art.

The term "primer" refers to an oligonucleotide, whether naturally occurring or synthetically produced, which is capable of acting as a point of initiation of synthesis when placed under conditions in which synthesis of a primer extension product complementary to a nucleic acid strand is induced. Such conditions include the presence of nucleotides (such as the four standard deoxyribonucleotide triphosphates) and an agent for polymerization such as a DNA polymerase, suitable temperature and pH, and other suitable reagents such as a source of magnesium or manganese ions.

One or more primers can be used in the amplification according to this invention each primer specific for a particular nucleic acid, but at least one primer is used which is complementary to the targeted nucleic acid, except for a single mismatch at or near the 3' end as defined herein. This critical primer has a thymine base in the position of the mismatch. Thus, the advantage of this invention is that with the use of such a primer, it is more likely that a mismatch between the target nucleic acid sequence and primer will be overcome and amplification will proceed efficiently. Thus, while ideal conditions would have all primers completely complementary to the predetermined nucleic acid, it is more likely, especially with certain viral DNAs, that mismatches will exist, and the need for the present invention will be evident. By the term "at or near the 3' end of the primer" is meant the mismatch occurs within four nucleotides of the 3' end of the primer. Preferably, the primer has a thymine base located at the 3' end or one nucleotide position away from it. Most preferably, it is at the 3' end.

While at least one primer must have the nucleotide with the thymine base as defined above, it is not essential that all primers used in the amplification reaction be so constructed. It other words, in amplification of DNA, both strands are amplified with primers and the amplification process. It is possible that a mismatch will occur with only one of the strands, or with both strands. The primers can thus be fashioned to accommodate as many mismatches that may be present. Where no mismatch occurs between a strand and primer, the primer need not have a thymine at or near the 3' end unless it is there for standard complementary.

Primers are generally single-stranded. The exact length of each primer will vary depending upon the use contemplated, the complexity of the target sequence, reaction temperature and the source of the primer. Generally, the primers used in this invention will have from 15 to 50 nucleotides, and preferably, they have from 20 to 30 nucleotides.

Primers useful herein can be obtained from a number of sources or prepared using known techniques and equipment, including for example, an ABI DNA Synthesizer (available from Applied Biosystems) or a Biosearch™ 8600 Series, 8700 Series or 8800 Series Synthesizer (available from Milligen-Biosearch, Inc.) and known methods for their use. Naturally occurring primers isolated from biological sources are also useful (such as restriction endonuclease digests).

Once the targeted DNA has been extracted (if necessary) and denatured, its strands are contacted with the primer composition described herein under conditions such that a mixture of hybridized products of primers and target DNA strands are formed. Such conditions are those normally used for amplification as described in U.S. Pat. No. 4,683,202 (noted above). Primer extension products are then formed with at least one of the hybridized products followed by additional priming and extension product formation. After denaturation (that is, separation of complementary products), the replicated target nucleic acid can be isolated from the reaction mixture using standard procedures and equipment. Preferably, at least one of the replicated nucleic acids is biotinylated.

The present invention is also useful for the detection of a specific nucleic acid having two complementary strands. Most nucleic acid sequences of interest already are double-stranded, such as those found in DNA. However, single-stranded nucleic acid sequences, such as mRNA, can be similarly detected after they are converted to a double-stranded sequence using reverse transcriptase.

A predetermined nucleic acid sequence is reproduced using a nucleic acid containing that sequence as a template. If the nucleic acid contains two strands, it is necessary to separate the strands, either as a separate step or simultaneously with the formation of primer extension products. Denaturing can be accomplished using any suitable physical, chemical or enzymatic means as described in the art. Heating to a suitable temperature is a preferred means.

Once the separated strands are available for use, synthesis of additional nucleic acid strands can be carried out using the primers in a buffered aqueous solution generally at a pH of from about 7 to about 9. Preferably, a molar excess of the primers is added to the buffered solution, and specific amounts are taught in the art (for example, in U.S. Pat. No. 4,683,202). The deoxyribonucleotide triphosphates dATP, dCTP, dGTP and dTTP are also added to the synthesis mixture in adequate amounts and the resulting solution is heated to about 90°-100° C. for up to 10 minutes, and preferably from about 1 to about 4 minutes. After this heating, the solution is preferably cooled to room temperature, and an appropriate agent for inducing (or catalyzing) the formation of primer extension products is introduced. This inducing agent is generally known in the art as a polymerization agent. Reaction to form these products is carried out under known conditions (generally from room temperature to that temperature at which polymerization no longer occurs).

The polymerization agent may be any compound, or combination of reagents, which will function to accomplish the synthesis of primer extension products, including enzymes (for example, E. coli DNA polymerase I, T4 DNA polymerase, Klenow polymerase, reverse transcriptase and others known in the art). Particularly useful enzymes are thermally stable enzymes, cloned or naturally occurring, such as those obtained from various Thermus bacterial species. Other polymerization agents are described in U.S. Pat. No. 4,683,202.

Preferred thermally stable enzymes are DNA polymerases isolated from from Thermus aquaticus or synthetically prepared by cloning methods as described in EP-A-0 258 017 (published Mar. 2, 1988). Those polymerases generally have a molecular weight of about 86,000–90,000 daltons. Other useful enzymes are described by Rossi et al, *Syst. Appl. Microbiol.* 7(2-3), pp. 337-341, 1986. Generally, the synthesis of extension products will be initiated at the 3' end of each primer and proceed in the 5' to 3' direction along the template until synthesis is terminated.

The newly formed primer extension products comprising the newly synthesized strands and their respective primers form double-stranded molecules with the initial target strands which are used in the succeeding steps of the method. These strands are then separated by denaturation as described above to provide single-stranded molecules, onto which new nucleic acids are synthesized as described above. Additional reagents may be needed to keep the amplification procedure going, after which most of the extension products will consist of the specific nucleic acid sequence bounded by the primers (that is, complementary products).

The steps of strand separation and extension product synthesis can be repeated as often as needed to produce the desired quantity of the specific nucleic acid needed for the use, for example detection. Generally, the sequence of steps is repeated at least once, and preferably at least 5 to 50 times.

When it is desired to produce more than one specific nucleic acid from the first nucleic acid or a mixture thereof, the appropriate number of sets of primers are used in the general procedure described above.

Generally, once a desired amount of the nucleic acid sequence of interest has been generated and the primer extension products are separated for a last time, the primer extension products (including the biotinylated ones) are contacted with an oligonucleotide probe designed to either capture the or detect the products.

In one embodiment, the probe is designed to capture or insolubilize the products. Thus, the probe is immobilized or capable of being immobilized on a solid phase of some type, such as membranes, filters, films, slides, particles, microtiter plates or any other suitable solid material readily apparent to one skilled in the art. Preferably, the solid phase is a polymeric particle (as defined in more detail below). The oligonucleotide may be attached covalently, or adsorbed, to the solid phase using teaching known in the art for such attachment. For example, one method of covalent attachment is through reaction of certain linking moieties which are described in U.S. Ser. No. 104,200 (filed Oct. 2, 1987 by Levenson et al), now U.S. Pat. No. 4,914,210 (issued Apr. 3, 1990).

Polymeric particles useful as solid phases for capture can be composed of any suitable polymeric material which is water-insoluble, and which provides the necessary surface reactive groups for attaching an oligonucleotide directly or indirectly. Thus, the surface reactive groups can be, for example, sulfhydryl, amino, active halogen atoms, epoxy groups, isocyanate, aziridine, activated 2-substituted ethylsulfonyl, vinylsulfonyl, active aldehyde, 2-substituted ethylcarbonyl, carboxy and others which will react with the respective sulfhydryl, amino or hydroxy groups of the linking group.

Particularly useful particles are composed of polymers prepared from ethylenically unsaturated polymerizable monomers, at least one of which has an active halogen atom, activated 2-substituted ethylsulfonyl, carboxy or vinylsulfonyl group. Representative monomers are known in the art and would be readily apparent to one skilled in the art. Particularly useful monomers include those having reactive carboxy groups, such as acrylic acid and methacrylic acid.

In the embodiment described above, it is preferred that one of the primers be biotinylated so that it can be reacted with an avidin-enzyme conjugate for subsequent detection. That is, the primer has a biotin moiety covalently attached thereto. Such conjugates of primer and biotin can be readily prepared using known technology.

The insoluble hybridized product of probe and biotinylated primer extension product can be separated from soluble materials using any suitable separation means, including centrifugation, filtration and washing. Preferably, a microporous filtration membrane is used. Particularly useful microporous filter membranes include polyamide membranes marketed by Pall Corp. (for example as Ultipore™, Loprodyne™ or Biodyne™ membranes).

The membranes can be used as a separate substrate with suitable containers for collecting fluid and soluble materials. Preferably, however, they are mounted as part of a test device. Various test devices are known in the art including those described in U.S. Pat. No. 3,825,410 (issued Jul. 23, 1974 to Bagshawe), 3,888,629 (issued Jun. 10, 1975 to Bagshawe), 3,970,429 (issued Jul. 20, 1976 to Updike) and 4,446,232 (issued May 1, 1984 to Liotta). Particularly useful devices are described in EP-A-0 308 231 (published Mar. 22, 1989), and in copending U.S. Ser. No. 339,923 (filed Apr. 17, 1989 by Schnipelsky et al).

The insoluble hybrid collected is contacted with a peroxidase-avidin conjugate which complexes with the biotinylated portion of the hybrid. Useful conjugates are commercially available from a number of sources. It usually requires a few minutes for the complexation to occur and uncomplexed conjugate passes through the membrane along with any fluid.

Following this, the reaction product is contacted with a composition which provides a dye in the presence of the enzyme label used. In a preferred embodiment, avidin is conjugated with peroxidase, and a dye-providing composition useful with peroxidase and hydrogen peroxide is used.

Useful dyes or dye-providing reagents are known in the art for a given enzyme. For example, useful dye-providing reagents for peroxidase include tetramethylbenzidine and derivatives thereof, and leuco dyes, such as triarylimidazole leuco dyes (as described in U.S. Pat. No. 4,089,747, issued May 16, 1978 to Bruschi). Particularly useful dye-providing compositions include triarylimidazole leuco dyes used in combination with certain stabilizing materials, for example described in U.S. Ser. No. 136,166 (filed Dec. 18, 1987 by McClune et al).

The presence of the dye in the insoluble material is an indication of the presence of the targeted DNA in the speciment tested. The dye can often be observed visually without the use of equipment, but in some instances, the dye density may be faint or outside the visible region of the electromagnetic spectrum, and thus require suitable detection equipment (that is, spectrophotometers) for adequate determination. Procedures for doing this are well known in the art.

Alternatively, the solid phase, such as the polymeric particles, can be labeled in a suitable manner (for example, using dyed or radioactive particles) and a biotinylated primer is unnecessary. Detection of the primer extension products is achieved by isolating the insoluble complexed products and detecting the labeled solid phase visually or with suitable equipment.

In another embodiment, biotinylated primer can be used which will complex with a solid phase comprising avidin either adsorbed or covalently bound to the solid phase. Thus, the avidin-biotin complex is used for capture, rather than labeling. Other specific binding reactions can be similarly used, as described in U.S. Ser. No. 273,779 (filed Nov. 21, 1988 by Burdick et al), incorporated herein by reference. In this embodiment, a detection probe is used to provide a label to detect the resulting insoluble product. The probe is complementary to one of the primer extension products, and can be labeled with any suitable label, including chromogenic or fluorogenic moieties, chemiluminescent moieties, radiolabels, enzymes, ferritin, magnetizable particles, and others readily apparent to one skilled in the art. The label can be directly attached to the probe, or indirectly through a linking group or specific binding complex. For example, while an avidin-biotin reaction may be used for capture in this embodiment, an antibody-haptan reaction may be useful to attach a label to a probe. Other embodiments are well within the purview of one skilled in the art in view of this teaching.

The method of this invention can be used to amplify or detect nucleic acids associated with infectious diseases, genetic disorders or cellular disorders such as cancers. Various infectious diseases can be diagnosed by the presence of a small quantity of DNA in a clinical specimen specific to an organism, such as a bacterium, yeast, protozoan or virus. Retroviruses are detected to advantage with the present invention, with HIV-I being a retrovirus of particular interest.

In a preferred embodiment, a method for the detection of at least one predetermined nucleic acid having two complementary strands comprises:

A. denaturing the complementary strands of a double-stranded nucleic acid in a biological specimen, B. contacting the specimen with a primer composition, the primer composition consisting essentially of a primer which is complementary to a sequence of one of the nucleic acid strands in every position except a single position at or near the 3' end of the primer, resulting in a single mismatch at the single position between the primer and the nucleic acid strand, the primer having a nucleotide with a thymine base in the position of the mismatch, the specimen also simultaneously contacted with one or more additional primers which are substantially complementary to the other strand of the nucleic acid, so as to form hybridized products of the primers and the nucleic acid strands, C. in the presence of a thermostable polymerase, and the deoxyribonucleotide triphosphates dATP, dCTP, dGTP and dTTP, forming extension products of the primers in the hybridized products, which extension products, when separated from their complements, can serve as templates for synthesis of the extension products of the primers, D. separating the primer extension products from the templates on which they were synthesized, E. contacting the separated extension products and the predetermined nucleic acid with additional primers complementary to the strands, resulting in amplification of the nucleic acid to form complementary products, F. separating the primer extension products from the complementary products formed in step E, G. contacting at least one primer extension product separated in step F with an oligonucleotide probe which is labeled for detection or capture and is complementary thereto to form a complementary product of the probe and the primer extension product, and H. detecting the complementary product formed in step G as an indication of the presence of the predetermined nucleic acid in the specimen.

The following example illustrates the practice of this invention, but is not meant to be limiting in any way.

Example 1

Effect of Using Primers in PCR Amplification Having Mismatches at 3' End Using High Magnesium Salt Concentration in Amplification This example illustrates the invention whereby primers having nucleotides with a thymine base at the 3' end provide efficient amplification as compared to primers having other bases at the 3' end in the presence of mismatches with the target nucleic acid.

Primers

The nucleotides in the primers, probe and target nucleic acid are designated by the standard abbreviations of T for thymine, A for adenine, G for guanine and C for cytosine. There are twelve possible mismatches between primer and target which can occur at the 3'-end. Four of them are symmetrical (that is, A-A, G-G, C-C and T-T) and eight are asymmetrical (A-C, C-A, C-T, T-C, G-A, A-G, T-G and G-T). The first letter designates the nucleotide on the primer and the second letter designates the nucleotide on the target nucleic acid.

We studied these twelve mismatches as well as correct pairings using a set of primers having almost identical 28 base sequence except for the base at the 3' end. The primers were prepared using the SK-38 primer, which is routinely used for HIV-I DNA amplification (gag region), as the basis for the sequence. The SK-38 primer was prepared using an automated synthesizer and known phosphoramidite chemistry. This primer was first varied at the 3' end to produce three of the twelve possible mismatches with the target nucleic acid. It was then shifted one position to the right, resulting in a different 3' end, and then three more mismatch variations were prepared by making substitutions at the end. This procedure was repeated twice, once by shifting SK-38 one position to the left, and once by shifting it four positions to the left. The sequences of the resulting primers are shown in the following Table.

TABLE

| Oligonucleotide | Oligonucleotide Sequences Nucleotide Base Sequence | Primer 3' End | Corresponding Template Base |
|---|---|---|---|
| Template | 3'-TGTTTATTAGGTGGATAGGGTCATCCTCTTTAG-5' | | |
| Primer 1 (SK-38) | 5'-ATAATCCACCTATCCCAGTAGGAGAAAT-3' | T | A |

TABLE-continued

Oligonucleotide Sequences

| Oligonucleotide | Nucleotide Base Sequence | Primer 3' End | Corresponding Template Base |
|---|---|---|---|
| Primer 2 | ATAATCCACCTATCCCAGTAGGAGAAAC | C | A |
| Primer 3 | ATAATCCACCTATCCCAGTAGGAGAAAG | G | A |
| Primer 4 | ATAATCCACCTATCCCAGTAGGAGAAAA | A | A |
| Primer 5 | AATAATCCACCTATCCCAGTAGGAGAAA | A | T |
| Primer 6 | AATAATCCACCTATCCCAGTAGGAGAAC | C | T |
| Primer 7 | AATAATCCACCTATCCCAGTAGGAGAAG | G | T |
| Primer 8 | AATAATCCACCTATCCCAGTAGGAGAAT | T | T |
| Primer 9 | TAATCCACCTATCCCAGTAGGAGAAATC | C | G |
| Primer 10 | TAATCCACCTATCCCAGTAGGAGAAATG | G | G |
| Primer 11 | TAATCCACCTATCCCAGTAGGAGAAATA | A | G |
| Primer 12 | TAATCCACCTATCCCAGTAGGAGAAATT | T | G |
| Primer 13 | ACAATAATCCACCTATCCCAGTAGGAG | G | C |
| Primer 14 | ACAATAATCCACCTATCCCAGTAGGAC | C | C |
| Primer 15 | ACAATAATCCACCTATCCCAGTAGGAT | T | C |
| Primer 16 | ACAATAATCCACCTATCCCAGTAGGAA | A | C |

All of the primers were synthesized on a Biosearch ™ 8700 Synthesizer using standard phosphoramidite chemistry. They were purified by polyacylamide gel electrophoresis and desalting. Base composition analysis was used to assess the purity and composition of the primers. Stock solutions were prepared in TE buffer (described below) using optical density measurements to adjust concentration.

Materials

The avidin-bead reagent used was prepared as described in EP-A-0 302 715 (published Feb. 8, 1989) using particles of poly[styrene-co-m & P-(2-chloroethylsulfonylmethyl)styrene] (95.5:4.5 molar ratio) having an average diameter of about 2.0 μmeters, stored in a suspension (0.45 weight % solids) in glycine buffer (0.1 molar, pH 8.5).

The DNA polymerase used was isolated from *Thermus aquaticus* having an activity of about 4 units/μl.

A SSPE solution contained Triton ™ X-100 nonionic surfactant (0.2 weight %) and phosphate buffered saline solution (8.5 mmolar, pH 7) containing sodium chloride (149 mmolar) and ethylenediaminetetraacetic acid (1 mmolar).

A diluent solution comprised 360 mmolar sodium chloride, 20 mmolar sodium dihydrogen phosphate (pH 7.4) and 2 mmolar ethylenediaminetetraacetic acid and Triton ™ X-100 nonionic surfactant (0.2 weight %).

The TE buffer contained tris(hydroxymethyl)aminomethane hydrochloride buffer (10 mmolar) and ethylenediaminetetraacetic acid (1 mmolar), with pH adjusted to 8 using hydrochloric acid.

The PCR buffer contained tris(hydroxymethyl)aminomethane (10 mmolar, pH 8), potassium chloride (50 mmolar) and magnesium chloride (10 mmolar).

A buffer identified as the "running buffer" (pH 8) used for electrophoresis was composed of tris(hydroxymethyl)aminomethane buffer (89 mmolar), boric acid (89 mmolar) and ethylenediaminetetraacetic acid (2 mmolar).

A leuco dye composition for detection was prepared with 2-(4-hydroxy-3,5-dimethoxyphenyl)-4,5-bis(4-methoxyphenyl)imidazole as follows: solid leuco dye (to make a 0.1 weight % solution) was dissolved in a solution of poly(vinyl pyrrolidone) (20 weight %) in sodium phosphate buffer (5 mmolar). This solution was then added to a solution containing hydrogen peroxide (10 mmolar), 4'-hydroxyacetanilide (5 mmolar) and diethylenetriaminepentaacetic acid (10 μmolar) in sodium phosphate buffer to produce a final concentration of 1 weight % polymer and 0.005 weight % leuco dye.

The Surecell ™ (Eastman Kodak Co.) disposable test devices used in the assays contained a Biodyne ™ nylon microporous membrane (Pall Corp). in each test well. The membranes were treated with succinylated casein (1 g/m²) prior to use.

The probe used in the assays was prepared according to procedure described in copending U.S. Ser. No. 406,224 (filed on even date herewith by Warren III and Oakes) and entitled "An Oligonucleotide-Enzyme Conjugate and a Method for Its Preparation". This probe had the following structure:

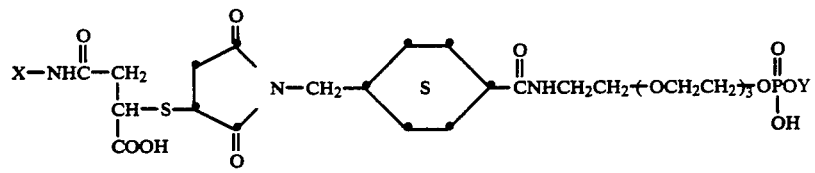

wherein X—NH— is the residue of horseradish peroxidase, and Y is the oligonucleotide chain having the sequence:

5'—GAGTGATGAGGAAGAGGAGGGTG—3'

The predetermined DNA fragment detected in the assays was a 180 nucleotide segment of the gag region (core protein) of the HIV-I genome cloned into a derivative of M13 vector and prepared using standard procedures.

The biotinylated primer used in the assay had the following nucleotide sequence:

5'—X—TTTGGTCCTTGTCTTATGT-
CCAGAATGC—3' wherein X represents a biotintetraethylene glycol spacer arm prepared and attached as described in U.S. Ser. No. 104,200 (noted above).

Assay

Amplification was carried out using a Cetus/Perkin-Elmer thermocycler in microfuge tubes using 100 μl solutions containing the following: target fragment ($10^{-16}$ molar), primers (1 μmolar each), polymerase (7.5 units/100 μl), dNTPs (6 mmolar total), magnesium chloride (10 mmolar) and PCR buffer.

The thermal profile for amplification was a 5 minute cycle carried out 30 cycles as follows:

| | |
|---|---|
| 70° C. rising to 94–95° C. | 1 minute |
| 94–95° C. | 0.5 minute (denature) |
| 94–95° C. lowering to 55° C. | 1.25 minutes |
| 55° C. | 0.5 minute (hybridize) |
| 55° C. to 70° C. | 0.75 minute |
| 70° C. | 1 minute (extend primers) |

Detection of the amplified target was accomplished in two different ways. Agarose gel electrophoresis was used to identify that a fragment of the expected size was synthesized. The sequence information was confirmed by hybridization with a horseradish peroxidase-labeled oligonucleotide probe.

Gel electrophoresis was carried out as follows: aliquots (6 μl) of the PCR reaction mixture were withdrawn and applied to 4% agarose gels (3% NuSieve ™ and 1% SeaKem ™, available from FMC Bio-Products). The gels were prestained with an ethidium bromide solution (4 μl, 10 mg/ml). The "running buffer" (600 μl) also contained ethidium bromide (24 μl). The gels were electrophoresed at 160 volts/cm for one hour, then photographed and the resulting bands visualized.

Hybridization with the probe was carried out as follows:

PCR reaction product (5 μl of a 1:10 dilution in diluent solution in a 1.5 ml microcentrifuge tube) was melted at 95° C. for 5 minutes, spun briefly in the microfuge, then mixed with the avidin-bead reagent (2 μl) and the peroxidase-labeled probe (1 pmolar in 3 μl), and incubated at 42° C. for five minutes. Diluent solution (50 μl) was added, mixed and the solutions were added to the test wells of Surecell ™ test devices, and fluid was allowed to flow through the membranes in the test wells.

The test wells were washed with a wash solution [50 μl of a 1:10 dilution of diluent solution in phosphate buffer (pH 7)] which had been prewarmed to 55° C. for 30 minutes. Washing was repeated four times.

The leuco dye composition (100 μl) was added and after two minutes the dye on the membrane was visually scored using a color chart (values 1 to 5, with 5 being the highest density). FIG. 1 shows a summary matrix of both gel electrophoresis and probe hybridization results for each assay using the various primers. The letters "A", "C", "G" and "T" are used in all Figures to represent nucleotides in the nucleic acids or primers, which nucleotides have bases corresponding to adenine, cytosine, guanine and thymine, respectively.

The electrophoresis results are shown as either positive (+) or negative (−). The probe results are shown as the color chart value corresponding to dye density observed. All of the results are the average of two replicates.

These data show that where the primers have a nucleotide with a thymine base at the 3' end, amplification efficiency remains high as evidenced by the positive electrophoretic results and generally higher dye densities. Where primers ended in nucleotides having adenine, guanine or cytosine bases, amplification was weak or nonexistent. This indicates that the use of the primers according to this invention will overcome mismatches at or near the 3' end of the primer more readily than other primers.

EXAMPLE 2

Effect of Using Primers in PCR Amplification Having Mismatches at 3' End Using Low Magnesium Salt Concentration in Amplification The amplification procedures of Example 1 were repeated using the same materials except that the amount of magnesium chloride used in the amplification reaction was 2.5 mmolar instead of 10 mmolar, and the dNTPs were present in a total amount of 600 μmolar instead of 6 mmolar. This lower concentration has been designated a "low salt" concentration for distinguishing various amplification reaction procedures.

FIG. 2 shows the results of gel electrophoresis and hybridization with a detectable probe, as described in Example 1. These results again confirm the advantages of this invention as pointed out above, except it is apparent also that the amount of magnesium chloride concentration did not affect the results. This result was unexpected since the concentration of magnesium chloride often affects amplification reactions.

EXAMPLE 3

Effect of Using Primers in PCR Amplification Having Mismatches at 3' End Using High Magnesium Salt Concentration and Low Hybridization Temperature in Amplification This example was carried out exactly as Example 1 except that the hybridization temperature in the amplification cycles was 40° C. instead of 55° C.

The results are shown in FIG. 3 wherein agarose gel electrophoresis and hybridization with a detectable probe indicate that the primers having a nucleotide with a thymine base at the 3' end are highly useful for efficient amplification despite mismatches at the 3' end as compared to other primers.

The invention has been described in detail with particular reference to preferred embodiments thereof, but it will be understood that variations and modifications can be effected withinthe spirit and scope of the invention.

We claim:

1. A method for amplifying at least one nucleic acid, said method comprising:
   A. contacting a specimen comprising a nucleic acid with a primer composition,
      said primer composition consisting essentially of a primer which is complementary to a sequence of said nucleic acid in every position of said sequence except a single position at the 3' end of said primer, resulting in a single mismatch at said single position between said primer and said nucleic acid sequence,
      said primer having a nucleotide with a thymine base in the position of said mismatch, and
   B. substantially simultaneously, contacting said specimen with a DNA polymerase under conditions such that said nucleic acid is amplified in the resulting mixture by forming primer extension products, and denaturation of said primer extension products, said product formation and denaturation being carried out at least five times.

2. The method of claim 1 for the amplification of viral DNA.

3. The method of claim 2 for the amplification of HIV-I-DNA.

4. A method for the detection of a target nucleic acid, said method comprising:
   A. contacting a specimen comprising a nucleic acid with a primer composition,
      said primer composition consisting essentially of a primer which is complementary to a sequence of said nucleic acid in every position of said sequence except a single position at the 3' end of said primer, resulting in a single mismatch at the single position between said primer and said nucleic acid sequence,
      said primer having a nucleotide with a thymine base in the position of said mismatch,
   so as to form hybridized products of said primer and said nucleic acid,
   B. forming primer extension products in said hybridized products, priming, extending and amplifying said primer extension products using a DNA polymerase in a polymerase chain reaction,
   C. separating the resulting primer extension products and contacting them with a detection or capture oligonucleotide probe to form a complementary product, and
   D. detecting the presence of said complementary product as an indication of the presence of said target nucleic acid in said specimen.

5. The method of claim 4 using a capture oligonucleotide and detection is accomplished using a biotinylated primer and an avidin-enzyme conjugate.

6. The method of claim 5 wherein said conjugate comprises peroxidase.

7. The method of claim 6 for the detection of HIV-I DNA.

8. The method of claim 4 wherein detection is accomplished using a probe which is labeled or capable of being labeled with an enzyme.

9. The method of claim 8 wherein said enzyme is peroxidase, and said detection is carried out using a composition which provides a dye in the presence of peroxidase and hydrogen peroxidase.

10. The method of claim 4 wherein one of said primers is either attached to or capable of being attached to an insoluble substrate.

11. A method for the detection of at least one predetermined nucleic acid having two complementary strands comprises:
   A. denaturing the complementary strands of a double-stranded nucleic acid in a biological specimen,
   B. contacting said specimen with a primer composition, said primer composition consisting essentially of a primer which is complementary to a sequence of one of said nucleic acid strands in every position of said sequence except a single position at the 3' end of said primer, resulting in a single mismatch at said single position between said primer and said nucleic acid strand, said primer having a nucleotide with a thymine base in the position of said mismatch,
   said specimen also simultaneously contacted with one or more additional primers which are substantially complementary to the other strand of said nucleic acid,
   so as to form hybridized products of said primers and said nucleic acid strands,
   C. in the presence of a thermostable polymerase, and the deoxyribonucleotide triphosphates dATP, dCTP, dGTP and dTTP, forming extension products of said primers in said hybridized products, which extension products, when separated from their complements, can serve as templates for synthesis of said extension products of said primers,
   D. separating said primer extension products from the templates on which they were synthesized,
   E. contacting said separated extension products and said predetermined nucleic acid with additional primers complementary to the strands, resulting in amplification of said nucleic acid to form complementary products,
   F. separating said primer extension products from the complementary products formed in step E,
   G. contacting at least one primer extension product separated in step F with an oligonucleotide probe which is labeled for detection or capture and is complementary thereto to form a complementary product of the probe and said primer extension product, and
   H. detecting the complementary product formed in step G as an indication of the presence of said predetermined nucleic acid in the specimen.

12. The method of claim 11 for the detection of HIV-I DNA in whole blood or semen.

13. The method of claim 11 carried out by repeating steps E and F from 5 to 50 times before performing step G.

14. The method of claim 11 wherein more than one nucleic acid forms a single mismatch with its primer.

15. The method of claim 1 wherein said polymerase is isolated from Thermus aquaticus or is prepared using recombinant means.

16. The method of claim 6 wherein said polymerase is thermostable and is isolated from Thermus aquaticus or is prepared using recombinant means.

* * * * *